United States Patent [19]

Datta et al.

[11] Patent Number: 5,532,148

[45] Date of Patent: Jul. 2, 1996

[54] PROCESS FOR PRODUCING OF CITRIC ACID AND MONOVALENT CITRATE SALTS

[75] Inventors: Rathin Datta, Chicago; Eugene P. Bergemann, Hoffman Estates, both of Ill.

[73] Assignee: NTEC, Inc., Hoffman Estates, Ill.

[21] Appl. No.: 521,210

[22] Filed: Aug. 30, 1995

[51] Int. Cl.$^6$ .................................................. C12P 7/48
[52] U.S. Cl. .................... 435/144; 435/136; 435/800; 435/917
[58] Field of Search ................................. 435/144, 917, 435/136, 803

[56] References Cited

U.S. PATENT DOCUMENTS

| | | | |
|---|---|---|---|
| 3,622,455 | 11/1971 | Iizuka et al. | 435/146 |
| 3,886,041 | 5/1975 | Kabil | 435/146 |
| 3,941,656 | 3/1976 | Hustede et al. | 435/146 |
| 4,155,811 | 5/1979 | Nobel et al. | 435/146 |
| 4,278,764 | 7/1981 | Rottigni et al. | 435/146 |
| 4,391,908 | 7/1983 | Tabvchi et al. | 435/146 |
| 5,081,025 | 1/1992 | Kirkovits et al. | 435/146 |
| 5,104,799 | 4/1992 | Mothes et al. | 435/144 |
| 5,149,643 | 9/1992 | Mothes et al. | 435/144 |

*Primary Examiner*—Herbert J. Lilling
*Attorney, Agent, or Firm*—Welsh & Katz, Ltd.

[57] ABSTRACT

A short process is disclosed for the production of citric acid in high yield and purity. Conidia of *Aspergillus niger* are cultured in an aqueous solution of decationized glucose syrup in a fermentation medium whose manganese(II) concentration is 2.5 to less than 20 parts per billion and whose pH value is about 1.5 to about 3.0. The fermentation medium is maintained for about 4–7 days to form citric acid and mycelia pellets in an aqueous product broth. That broth is filtered and then electrodialyzed to form a citric acid-containing aqueous broth. That broth is decolorized and ion-exchanged to remove color and inorganic ions and form an aqueous citric acid solution in which citric acid constitutes at least 98 percent of the organic acid present.

11 Claims, No Drawings

PROCESS FOR PRODUCING OF CITRIC ACID AND MONOVALENT CITRATE SALTS

TECHNICAL FIELD

This invention relates to a process for preparing citric acid, and more particularly to an economical process that produces citric acid of high purity and yield using fewer steps than are usually required.

BACKGROUND OF THE INVENTION

Citric Acid is produced worldwide by fermentation of carbohydrates followed by multi-step purification and recovery processes. Although many micro-organisms are known to produce citric acid, only two—Aspergillus niger a fungus, and Candida sp. a yeast, have been used for commercial production. Of the two—A. niger strains have been the organisms of choice. Many fermentation carbon sources have been used such as molasses; glucose syrups derived from hydrolyzed starch of corn, cassava, sweet potatoes and the like; glucose syrups derived from hydrolyzed cellulosic feedstocks, and also hydrocarbons and the like as are well known.

Under normal fermentation conditions, the A. niger strains do not produce citric acid in high yields or in high concentrations, often because of feed stock contamination. When molasses is used as the carbon source for example, many undesirable constituents have to be removed prior to use. Methods of molasses purification include use of ferrocyanide salts precipitation, ion-exchange, and carbon adsorption. When glucose syrup from starch sources are used, the purification steps to remove the undesirable constituents are less onerous but ion-exchange and/or adsorption are required.

Fermentation by A. niger in submerged culture also requires the development of the suitable inoculum. In many cases this involves inoculum propagation in multi-stage fermentors and very careful control of the concentration of potential pellet-forming mycelia in each of the propagation stages. In the production fermentation, mycelial pellets of approximately one millimeter (mm) diameter are formed and these pellets can produce high levels of citric acid with high yields.

If the environmental conditions in the fermentor are not carefully controlled, the acid production can be very adversely reduced. The key environmental control factors are: trace metal concentrations particularly iron, copper, zinc and manganese—maintenance of low but controlled levels (in parts per billion) of manganese is critical; pH value, nitrogen and phosphate levels. Often, control of the above factors and development of specific strains still fail to produce citric acid without contaminating organic acid impurities such as iso-citric, gluconic or oxalic acids. A good recent summary of citric acid production microorganisms is provided in Bigelis et al., Chapter 6 in *Food Biotechnology Microorqanisms*, Hui and Khachaturians eds., VCH Publishers, New York (1995) pp. 239 ff.

The conventional citric acid recovery and purification process is a unwieldy multi-step process that generates waste gypsum. That process usually involves ten steps, several of which are cumbersome solid-liquid separations.

Thus, the A. niger mycelia are separated from the fermentation broth by settling followed by rotary vacuum filtration where solid filter-aid is added to form a mycelia filter cake that can be disposed as animal feed. The filtered broth is then neutralized with high grade lime (0.5 lb/lb citric acid), and initially, the oxalate (if any is formed in the broth), is precipitated as the calcium salt and removed by filtration. The lime-containing slurry is then heated first to 80°–90° C. and then to 95° C., and the insoluble calcium citrate is recovered using a rotary filter.

The recovered calcium citrate solid is formed into an aqueous slurry and is then mixed with 95 percent sulfuric acid (0.8 lb/lb citric acid). The now soluble citric acid is removed from the calcium sulfate waste product by another rotary filtration. The citric acid in the sulfuric acid phase is present at a concentration of about 150–200 g/L, and that phase is concentrated in a multiple effect evaporator to approximately 67 weight percent, followed by treatment by ion exchange and/or activated carbon, further evaporation, and the desired citric acid is crystallized, washed and dried. A general description of such a conventional citric acid recovery and purification process is provided in Atkinson et al., Chapter 19 in Biochemical Engineering and biotechnology Handbook, 2nd Ed., Stockton Press, New York (1991) pp. 1098–1100.

The above process creates approximately two pounds of waste gypsum per pound of citric acid recovered. The gypsum cake wash also creates solid wastes in the wash waters. Furthermore, many large and unwieldy solid liquid filters are used and a large amount of energy is required in this multi-stage process that undergoes four phase changes.

For these reasons, many attempts have been made to eliminate the waste gypsum-based recovery and purification process. Liquid-liquid extraction using amine-containing ion exchangers has been used as one of the purification steps. Chromatography has been used to separate the carbohydrates from the organic acids. Although these techniques have met with some successes, they have not been able to produce efficient and relatively waste-free processes. Liquid ion exchange produces solvent-contaminated raffinates that have to be disposed of. The chromatographic separations produce more dilute streams than the feed, and hence the evaporation energy and costs increase. Often, the other organic acids produced by the particular fermentation interfere with the purification and do not produce the high purity citric acid desired.

Electrodialysis is a membrane based process in which ions are transported from one solution into another by application of an electrical driving force. Electrodialysis using desalting membranes has been used to recover salts of organic acids such as lactic, succinic and acetic from fermentation broths. See, for example, U.S. Pat. No. 5,143,834 whose disclosure is incorporated by reference and European Patent Application No. 90301838.1. In those processes however, fermentation produced the salts rather than the acids. The salts had to be further converted to the acids by use of electrodialysis with bipolar membranes, thereby requiring a two step process.

Furthermore any by-product acids produced could not be separated from the product acid by those processes. See, European Patent Application No. 90301838.1. Contrarily, fermentation produces citric acid in the broth, and that product has to be recovered and purified. Any by-product acids, if produced, lead to difficulties in purification because their properties and separation methods are substantially the same as that for the main product.

An improved process should be able to produce citric acid and/or its monovalent salts with high purity, without creating gypsum waste, without multiple phase changes, without organic solvents, require low energy and be of low overall cost. One such process has been discovered as is discussed below. That process involves the integration of an improved method of fermentation with electrodialysis (ED) as the primary means of recovery and purification.

BRIEF SUMMARY OF THE INVENTION

It has now been discovered that a colorless, highly pure citric acid or monovalent citrate salt, e.g., monosodium citrate, can be produced in high yield by (i) using a glucose syrup fermentation carbon source feed that is substantially free of metal cations (e.g., below about 100 pm) and is produced from a clean carbohydrate feedstock such as starch from corn, cassava, sago or the like, (ii) carefully controlling the concentration of certain metal ions such as manganese(II) in the fermentation medium, (iii) inoculating that medium with a particular amount of A. niger spores (conidia) as are produced by solid substrate fermentation, and (iv) recovering and purifying the citric acid thus produced by electrodialysis (ED) followed by polish purification to remove residual color and ions. The unique combination of inoculum propagation, fermentation, recovery and purification steps enables the process to succeed. This process does not produce waste gypsum, it does not have phase changes or use organic solvents for extraction.

In the process of the present invention, an A. niger strain capable of producing citric acid is propagated under controlled conditions to form spores (conidia) on a solid substrate such as agar and/or corn cobs. A carefully controlled spore inoculation (approximately $5 \times 10^5$ spores/mL) to the fermentation medium in which transition metal levels (particularly manganese at parts per billion levels) are controlled leads to formation of mycelia pellets and citric acid production without formation of other organic acids. The use of glucose syrup derived from clean carbohydrate feedstocks enables the careful control of the medium constituents, particularly the transition metal levels and undesirable proteins and organic acids.

The fermentation broth so produced is particularly suitable for citric acid recovery and purification by ED. The ED process concentrates the citric acid by approximately twofold, and substantially removes all the carbohydrates and proteins from the aqueous broth. Polish purification with adsorbents such as activated carbon and ion exchangers removes the color and ash from the broth and can produce a highly pure (>99 percent) and colorless aqueous citric acid stream. That stream can be further concentrated, and the citric acid crystallized if crystalline solid product is desired, or the citric acid can be converted to a monovalent salt such as monosodium citrate that can be produced as a liquid concentrate directly for use in detergent formulations.

More specifically, a process for preparing citric acid is contemplated that comprises the steps of:

(a) culturing Aspergillus Niger conidia at a concentration of about $1 \times 10^5$ to about $1 \times 10^6$ conidia/mL in an aqueous solution of decationized glucose syrup present at about 100 to about 200 g/L of medium to form a fermentation medium. That fermentation medium (i) contains salts suitable for germinating the conidia to form mycelia pellets in a submerged culture, (ii) contain about 2.5 to less than 20 parts per billion $Mn^{+2}$ ions and (iii) has a pH value of about 1.5 to about 3.0

(b) The fermentation medium is maintained at the above pH value and at a temperature of about 25° to about 35° C. under aerobic conditions for a time period of about 4 to about 7 days to form mycelia pellets in an aqueous product broth.

(c) The aqueous product broth is filtered to remove the mycelia pellets and form a clear, citric acid-containing aqueous broth.

(d) That citric-acid containing aqueous broth is electrodialyzed to form a citric acid-containing aqueous concentrate.

(e) The citric acid-containing aqueous concentrate is decolorized and ion-exchanged to remove color and inorganic ions therefrom and form an aqueous citric acid solution in which citric acid constitutes at least 98 percent of the organic acid present. Citric acid or sodium citrate is thereafter preferably recovered from that aqueous citric acid solution.

DETAILED DESCRIPTION OF THE INVENTION

A process of this invention involves the unique integration of culture propagation and fermentation steps with electrodialysis- (ED-)based separation and purification steps to produce a high yield of highly purified citric acid or monovalent citrate salt.

Any strain of A. niger capable of producing citric acid from carbohydrate is suitable for use in a contemplated process. Exemplary strains are those available from the American Type Culture Collection (12301 Parklawn Drive, Rockville, Md. 20852 USA) having accession numbers ATCC 1015, ATCC 11414 (also known as NRRL 2270) and ATCC 13794 (also known as NRRL 2001).

The spores (conidia) of the strain are inoculated on a solid substrate such as agar slants or ground corn cobs to which carbohydrates and nutrients are added in such a combination as to propagate the spores in a solid culture. The temperature can range between about 20° to about 35° C., preferably between about 25° to about 30° C., the humidity in the spore propagation vessels is maintained at a high level (near saturation, e.g., about 60 percent to saturation) so that the solid substrate does not dry out and the A. niger conidia grow and produce further spores.

It is important to provide a carbohydrate substrate for spore propagation that is not too readily consumed so that vegetative growth does not become predominant. Malt extract, for example, is a good carbohydrate substrate for this propagation. It is also important to have a complement of transition metal ions, e.g. $Zn^{+2}$, $Fe^{+3}$ and $Mn^{+2}$, in the spore-forming medium that is much higher than that is present in the liquid fermentation medium. Without that relatively high for example $Mn^{+2}$ ion concentration (about 10 to about 50 parts per million) transition metal ion concentration, the solid substrate propagation does not proceed satisfactorily to provide a high enough concentration of proper spores, while permitting an appropriately low (parts per billion) transition metal concentration in the aqueous liquid fermentation medium.

The spores (conidia) are washed from the solid substrate or the substrate is directly charged to the liquid fermentation medium. The number of spores inoculated is carefully controlled to be within a range between $1 \times 10^5$ and about $1 \times 10^6$ spores/mL, and an average of approximately $5 \times 10^5$ spores/mL. When this range is maintained, the fermentation proceeds well.

The transition metal concentrations other than that of manganese ($Mn^{+2}$) are those normally used for the culture of A.. niger. However, the concentration of $Mn^{+2}$ has to be controlled very carefully within a range between about 2.5 and less than 20 parts per billion (ppb). A concentration of about 3 to about 10 ppb is preferred. Too high a concentration leads to nonproducing fermentation and a completely dispersed mycelial mass, whereas too low a concentration provides a low productivity and conversion.

Control of the $Mn^{+2}$ and other transition metal ion levels is not easy. The glucose syrup has to be thoroughly ion-exchanged (decationized) to completely remove $Mn^{+2}$ ions. Exemplary ion-exchange resins for this purpose are sulfonated cross-linked polystyrenes that include Amberlite® IR-120 and Dowex® 50 that are available from Sigma Chemical Co., St. Louis, Mo. Sometimes this treatment is not sufficient and special chelating resins such as Eichrom's Diphonix™ (U.S. Pat. No. 5,281,631) available from Eichrom Industries, Inc., Darien, Ill. or Reillex™ HPQ available from N-Tec Solutions Inc. of Hoffman Estates, Illinois are employed to remove $Mn^{+2}$. The level of $Mn^{+2}$ ions that originates from the inoculum has to be taken into account in the fermentation medium, and the inoculum $Mn^{+2}$ ion content that is transferred has to be carefully controlled. Thus, starting with a clean decationized glucose syrup derived from various starchy feedstocks leads to appropriate control of the fermentation medium composition.

The fermentation is conducted under aerobic conditions in shaken, agitated or sparged vessels. The temperature and pH value are maintained between 25° to 35° C. and 1.5 to 3.0, respectively. Ammonium salts such as $(NH_4)_2SO_4$ or $NH_4NO_3$ are commonly used as a nitrogen source and other similarly well-known nutrients such as phosphates, trace elements and the like that are required for fermentation are carefully controlled.

The fermentation is maintained for a time sufficient for mycelia pellets to grow in submerged culture. This time period is usually about 4 to about 7 days and preferably about 5 to about 6 days. During this period of pellet growth and citric acid synthesis, the concentration of glucose decreases to about 20 g/L, and more preferably to about 5 g/L.

The fermentation medium thus produced is very suitable for the ED based recovery and purification process. The mycelia grow in the form of small pellets that can be separated by decantation and microporous or ultrafiltration, or by rotary vacuum filtration from the aqueous product broth. The filtered citric acid-containing aqueous broth is relatively clear and substantially free of other contaminating organic acids because impurities such as other organic acids are not produced under the inoculum propagation and fermentation conditions outlined before. The dissolved proteins, amino acids and inorganic salts are also substantially low (e.g. less than 10 g/L total protein is usually observed) because of the method of inoculum and feed media preparation.

When a filtered aqueous broth is electrodyalyzed using high efficiency membranes that have high rejection coefficients and low diffusivity for non-ionic and other impurities, a substantially pure citric acid-containing aqueous concentrate is produced in a single step that does not require bipolar membranes as in U.S. Pat. No. 5,143,834 or EPO 90 301838.1. That aqueous concentrate can be further purified by polish ion-exchange using a mixed bed resin such as Amberlite® IRN-15D, MB-1A or Dowex® MR-3 available from Sigma Chemical Co., and decolorizing adsorption with activated carbon to provide a colorless citric acid-containing aqueous solution in which citric acid constitutes at least 98 weight percent and preferably at least 99 weight percent of the organic acids; i.e., carbon-containing acids, present in the solution.

The citric acid-containing aqueous concentrate can be further concentrated to form an aqueous solution containing about 40 to about 80 weight percent citric acid, and the citric acid crystallized if solid, crystalline citric acid product form is required. Monovalent citrate salts such as monosodium citrate can also be directly produced by neutralization of the acid during the ED process step as with an alkali metal hydroxide such as sodium or potassium hydroxide, and a solution of a monovalent alkali metal citrate salt can be further polish-purified and concentrated for direct use in detergent formulations, or the salt recovered by crystallization.

EXAMPLE

The A. niger strain used for fermentation was ATCC 11414. The culture was grown on malt extract agar slants (pH 5.5). Spore inoculum was taken and diluted in an aqueous solution of 0.8 percent Tween® 80 [polyoxyethylene (20) sorbitan monooleate] to provide an initial concentration of $5 \times 10^5$ spores/mL in the shake flasks. The composition of medium: 140 g/L of glucose equivalents from decationized glucose syrup derived from enzymatic hydrolysis of starch (sago) or commercial glucose syrup derived from corn starch, 3.1 g/L $NH_4NO_3$, 0.15 g/L $KH_2PO_{4, 0.15}$ g/L NaCl, 1.1 g/L $MgSO_4$, 6.6 mg/L $ZnSO_4 \cdot 7H_2O$, 0.1 mg/L $FeCl_3$. The initial pH value was adjusted to 2.0 with dilute $H_2SO_4$.

The starch hydrolysates were prepared from commercially available sago starch and corn starch by enzymatic hydrolysis with alpha-amylase followed by glucoamylase. The hydrolysate that was more than 95 percent glucose was decationized by passage over cation exchange resin (Amberlite® IR-120) to remove the trace amounts of metal ions and was stored in clean siliconized glass vessels. Glucose syrups of similar quality can also be prepared from other starch sources such as cassava via such a hydrolysis and decationization process.

The $Mn^{+2}$ content of the fermentation ingredients was monitored as was the final $Mn^{+2}$ concentration in the inoculated fermentation medium by measurement using ion-coupled plasma spectroscopy (ICP). The $Mn^{+2}$ concentration of the fermentation medium was kept at approximately 5 ppb. A few fermentations were run without decationization of the glucose syrup and control of $Mn^{+2}$ content as negative controls. All fermentations were carried out in baffled 250 mL shake flasks at 30° C. for approximately 7 days.

The following Table 1 shows data from some of the fermentation results. In all the studies, carbohydrates and organic acids were measured by HPLC using cation exchange resin column, refractive index detector and standardized with 100 percent pure analytical grade reagents.

TABLE 1

| Shake Flask Fermentation (time = 160 hrs) | | | |
| --- | --- | --- | --- |
| Fermentation Number | Citric Acid (g/L) | Citric Acid Yield (% w/w) | Culture Morphology |
| a. high Mn (1–5 ppm) (negative controls) | 0 | 0 | filamentous |
| 1 | 61.3 | 56.5 | tight pellets |
| 2 | 59.1 | 61.8 | tight pellets |

None of the fermentations with positive results and a high citric acid yield produced other contaminating organic acids in measurable quantities by HPLC, so that the citric acid purity in these studies was greater than 99 percent of the organic acids present.

The above results clearly show that by careful control of the spore inoculum, the transition metal concentration (particularly that of $Mn^{+2}$) and fermentation conditions a good citric acid fermentation can be achieved with a very clean product broth.

The mycelial pellets were removed from the broth by filtration and processed by electrodialysis in a TS-2 (Tokuyama Corporation) electrodialysis stack. The cation and anion membranes used were Neosepta® CM-1 and AFN respectively. Current densities of 50 mA/cm² were used and high current efficiencies were achieved. The average power required for citric acid ED was estimated to be between 0.3 to 0.5 Kwh/kg.

Both citric acid or sodium citrate could be efficiently processed. The concentrated product from the ED step was analyzed by HPLC and found to have no contaminating organic acids, the residual carbohydrates and proteins were also very low. The product had a pale yellow color.

This product stream was passed over an activated carbon column and an ion-exchange column to remove the color and ash respectively. Then it was concentrated further by vacuum evaporation to approximately 30 percent citrate. The product was colorless and upon analysis by HPLC against known standards its purity was determined to be greater than 99 percent.

This series of studies show that by the unique combination of inoculum development, controlled fermentation as well as ED based recovery and purification process, a highly pure citric acid can be produced from carbohydrates.

The foregoing description and the examples are intended as illustrative and are not to be taken as limiting. Still other variations within the spirit and scope of this invention are possible and will readily present themselves to those skilled in the art.

We claim:

1. A process for preparing citric acid that comprises the steps of:
   (a) culturing *Aspergillus Niger* conidia at a concentration of about 1×10⁵ to about 1×10⁶ conidia/mL in an aqueous solution of decationized glucose syrup to form a fermentation medium, said fermentation medium (i) containing salts suitable for germinating said conidia and forming mycelia pellets in a submerged culture, (ii) containing about 2.5 to less than 20 parts per billion $Mn^{+2}$ ions and (iii) having a pH value of about 1.5 to about 3.0;
   (b) maintaining said fermentation medium at said pH value and at a temperature of about 25° to about 35° C. under aerobic conditions for a time period of about 4 to about 7 days to form mycelia pellets in an aqueous product broth;
   (c) filtering said product broth to remove said mycelia pellets and form a clear, citric acid-containing aqueous broth;
   (d) electrodialyzing said citric acid-containing aqueous broth to form a citric acid-containing aqueous concentrate; and
   (e) decolorizing and ion-exchanging said citric acid-containing aqueous concentrate to remove color and inorganic ions therefrom and form an aqueous citric acid solution in which citric acid constitutes at least 98 percent of the organic acid present.

2. The process according to claim 1 wherein the concentration of $Mn^{+2}$ ions in said fermentation medium is about 3 to about 10 parts per billion.

3. The process according to claim 1 wherein said decationized glucose syrup is present in said fermentation medium at a concentration of about 100 to about 200 g/L.

4. The process according to claim 1 wherein said fermentation is maintained for a time period of about 5 to about 6 days.

5. A process for preparing citric acid that comprises the steps of:
   (a) culturing *Aspergillus Niger* conidia at a concentration of about 1×10⁵ to about 1×10⁶ spores/mL in an aqueous solution of decationized glucose syrup present at about 100 to about 200 g/L to form a fermentation medium, said fermentation medium (i) containing salts suitable for the transforming said conidia into mycelia pellets in a submerged culture, (ii) containing about 3 to about 10 parts per billion $Mn^{+2}$ ions and (iii) having a pH value of about 1.5 to about 3.0;
   (b) maintaining said fermentation medium at said pH value and at a temperature of about 25° to about 35° C., under aerobic conditions for a time period of about 5 to about 6 days to form mycelia pellets in an aqueous product broth;
   (c) filtering said product broth to remove said mycelia pellets and form a clear, citric acid-containing aqueous broth;
   (d) electrodialyzing said citric-acid-containing aqueous broth to form a citric acid-containing aqueous concentrate; and
   (e) decolorizing and ion-exchanging said citric acid-containing aqueous concentrate to remove color and inorganic ions and form an aqueous citric acid solution in which citric acid constitutes at least 98 percent of the organic acids present.

6. The process according to claim 5 including the further step of concentrating said aqueous citric acid solution to form an aqueous solution containing about 40 to about 80 weight percent citric acid.

7. The process according to claim 6 including the further step of recovering the citric acid as crystals.

8. The process according to claim 5 including the further step of adjusting the pH value of said citric acid-containing aqueous broth of step (d) with an alkali metal hydroxide to form an aqueous solution of a monovalent alkali metal citrate salt.

9. The process according to claim 8 including the further step of concentrating the aqueous alkali metal monovalent citrate salt solution to form an aqueous solution containing said alkali metal citrate at a concentration of about 40 to about 80 weight percent as citric acid.

10. The process according to claim 9 including the further step of recovering said alkali metal monovalent citrate salt as crystals.

11. The process according to claim 5 wherein citric acid present in said aqueous citric acid solution constitutes at least 99 percent of the organic acids present.

* * * * *